United States Patent [19]

Murphy et al.

[11] Patent Number: 4,663,485

[45] Date of Patent: May 5, 1987

[54] PROCESS FOR PURIFYING 4-HYDROXYACETOPHENONE

[75] Inventors: Carl D. Murphy; Donna L. Keene; Daniel D. Lindley, all of Corpus Christi, Tex.

[73] Assignee: Celanese Corporation, New York, N.Y.

[21] Appl. No.: 888,197

[22] Filed: Jul. 22, 1986

[51] Int. Cl.$^4$ ............................................. C07C 45/84
[52] U.S. Cl. ................................. 568/319; 568/324; 423/484
[58] Field of Search ............... 568/319, 324, 410, 411; 423/483, 484; 203/62

[56] References Cited

U.S. PATENT DOCUMENTS

| | | | |
|---|---|---|---|
| 2,414,418 | 1/1947 | Lofton | 568/324 |
| 3,403,183 | 9/1968 | Dobraty et al. | 568/324 |
| 3,806,588 | 4/1974 | Hann | 423/484 |
| 4,433,173 | 2/1984 | Gupta et al. | 568/324 |
| 4,593,125 | 6/1986 | Davenport et al. | 568/319 |
| 4,607,125 | 8/1986 | Mott | 568/319 |

Primary Examiner—James H. Reamer
Attorney, Agent, or Firm—M. Turken; D. R. Cassady

[57] ABSTRACT

A process is provided for the distillation of a composition containing 4-hydroxyacetophenone and hydrogen fluoride in the presence of an alkane assisting solvent having from 4 to 16 carbon atoms e.g. n-hexane or n-octane. The process is carried out to obtain an overhead vapor containing alkane solvent and most of the hydrogen fluoride in the feed, and a liquid residue containing most of the 4-hydroxyacetophenone in the feed. The overhead vapor is condensed to form two immiscible phases, one containing a preponderance of hydrogen fluoride and the other a preponderance of alkane solvent, with the latter phase being returned to the distillation as reflux. The liquid residue also separates into two immiscible layers, one containing most of the 4-hydroxyacetophenone in the feed which is recovered and the other a preponderance of alkane solvent.

14 Claims, No Drawings

PROCESS FOR PURIFYING 4-HYDROXYACETOPHENONE

This invention relates to a process for purifying 4-hydroxyacetophenone.

BACKGROUND OF THE INVENTION

4-Hydroxyacetophenone (4-HAP) is a possible intermediate for a variety of products having a multiplicity of end uses. Thus, U.S. Pat. No. 4,524,217, issued June 18, 1985 to Davenport et al, discloses a process for using 4-HAP to make N-acetyl-para-aminophenol (APAP) better known as acetaminophen, which has wide use as an analgesic. Pending U.S. application Ser. No. 06/627,381, filed July 3, 1984, discloses the use of 4-HAP as an intermediate for the production of 4-acetoxyacetanilide (4-AAA) which can be used for the preparation of poly(ester-amide)s capable of forming an anisotropic melt phase and suitable for being formed into shaped articles such as moldings, fibers and films. In addition, 4-AAA may also be hydrolyzed to form APAP. Pending U.S. application Ser. No 06/633,831, filed July 24, 1984, discloses a process wherein 4-HAP is used to produce 4-acetoxybenzoic acid (4-ABA) which is also capable of being used directly to make polymers which can be formed into an anisotropic melt suitable for the formation of shaped articles. Moreover, 4-ABA can be hydrolyzed to 4-hydroxybenzoic acid (4-HBA) which can be used as an intermediate for the production of preservatives, dyes, and fungicides. Pending U.S. applications Ser. No. 06/661,552, filed Oct. 17, 1984, and Ser. No. 06/689,533, filed Jan. 7, 1985, disclose processes wherein 4-HAP is used as an intermediate for the production of hydroquinone (HQ) which has utility as a photographic developer, polymerization inhibitor, dye intermediate, and anti oxidant.

Various U.S. patent disclosures teach processes for the production of 4-HAP by the Friedel-Crafts acetylation of phenol utilizing hydrogen fluoride as catalyst and reaction conditions within certain prescribed ranges. These include pending applications Ser. Nos. 06/714,407 filed Mar. 21, 1985 and 06/721,007 filed Apr. 8, 1985 which show acetic anhydride as acetylating agent, 06/716,016 filed Mar. 26, 1985 which shows acetic acid as acetylating agent and 06/616,989, filed June 4, 1984 which shows various acetylating agents including both acetic acid and anhydride and also discloses the production of 4-HAP by the Fries rearrangement of phenyl acetate with hydrogen fluoride catalyst. The entire disclosures of these applications are incorporated herein by reference.

While the foregoing and similar processes have the advantage of producing 4-HAP in relatively high yields, the crude product before purification contains an amount of hydrogen fluoride (HF), most of which must be removed and recycled for reasons of economy, and also to obtain a 4-HAP suitable for subsequent use. Some of the HF may be removed by straight distillation under relatively mild conditions. However, because of the apparent formation of a stable and relatively high boiling complex of 4-HAP and HF, removal of sufficient HF necessary to obtain a 4-HAP of suitable purity requires distillation under vacuum at temperatures so high as to cause an unfavorable loss of 4-HAP due to polymerization or other side reactions. Thus, any process which achieves a satisfactory level of separation of HF from 4-HAP without undue loss of 4-HAP is very desirable.

Simons et al, Journal of the American Chemical Society, 62, 485 and 486 (1940) show the use of hydrogen fluoride as a condensing agent for various rearrangements and at page 486 show the Fries rearrangement of phenyl acetate to obtain p-hydroxyacetophenone.

Dann and Mylius in a dissertation included as part of a series of Reports from the Institute for Applied Chemistry of the University of Erlangen, received for publication on Jan. 7, 1954 and published in Annalen der Chemie 587 Band, pages 1 to 15, disclose the reaction of phenol and glacial acetic acid in the presence of hydrogen fluoride to produce 4-hydroxyacetophenone (4-HAP) in a yield of 61.6%. This reaction may be conventionally characterized as a Friedel-Crafts acetylation of phenol with acetic acid as the acetylating agent.

Simons et al, Journal of the American Chemical Society, 61, 1795 and 1796 (1939) teach the acylation of aromatic compounds using hydrogen fluoride as a condensing agent and in Table 1 on page 1796 show the acetylation of phenol with acetic acid to produce p-hydroxyacetophenone (4-HAP) in 40% yield.

Davenport et al, U.S. Pat. No. 4,524,217 discloses a process of making an N-acyl-hydroxy aromatic amine such as N-acetyl-para-aminophenol (APAP or acetaminophen) by reacting a hydroxy aromatic ketone such as 4-HAP with a hydroxylamine salt and a base to obtain the ketoxime of the ketone, e.g. 4-HAP oxime, and subjecting the ketoxime to a Beckmann rearrangement to form the N-acyl-hydroxy aromatic amine. The hydroxy aromatic ketone may be prepared by the Fries rearrangement of a phenolic ester, e.g. phenyl acetate or the Friedel-Crafts acylation of a phenolic compound, e.g. phenol, with an acylating agent, e.g. acetic acid or anydride, using hydrogen fluoride as a catalyst.

European Patent No. 102,297 teaches a process of recovering ortho-benzoyl benzoic acid, hydrogen fluoride and boron trifluoride from a complex of these compounds by subjecting the complex to the action of an inert solvent in a distillation column. The inert solvent may be a halogenated hydrocarbon such as methylene chloride or 1,2-dichloroethane, or a fluorinated aromatic hydrocarbon.

SUMMARY OF THE INVENTION

In accordance with this invention, a composition comprising 4-hydroxyacetophenone (4-HAP) and hydrogen fluoride (HF) is distilled in a column or other vessel in the presence of an alkane having about 4 to 16 carbon atoms as an assisting solvent. The vapor overhead comprises a major portion of the HF in the feed to the distillation vessel mixed with some alkane. Upon condensation, the overhead vapor forms immiscible HF-rich and alkane-rich phases which can be separated by decantation. A liquid residue containing alkane solvent and most of the 4-HAP in the feed and which may contain other heavy ends, such as 2-hydroxyacetophenone, separates into 4-HAP-rich and alkane-rich immiscible phases. The 4-HAP-rich phase is removed from the base of the vessel or column for further purification, if any, and utilization in subsequent processes. If desired the alkane-rich phase is returned to the distillation as vapor and/or liquid recycle.

DESCRIPTION OF SPECIFIC EMBODIMENTS

The compositions containing 4-HAP and HF which are treated to separate these components utilizing the process of this invention are obtained, for example, as effluents from the production of 4-HAP by the Fries rearrangement of phenyl acetate or the Friedel-Crafts acetylation of phenol using HF as catalyst as taught, for example in the previously cited patent disclosures. In most cases, such compositions contain a molar preponderance of liquid HF in which is dissolved a product of reaction composed primarily of 4-HAP together with minor amounts of impurities such as 2-hydroxyacetophenone, phenol, and phenyl acetate. Depending on the nature of the process used to produce it, the amount of 4-HAP in the composition, excluding the HF, may be, for example in the range of about 25 to 98 weight percent, while the mole ratio of HF to 4-HAP plus impurities may be, for example about the same as the mole ratio of HF to phenyl acetate or phenol in the Fries rearrangement of phenyl acetate or Friedel-Crafts acetylation of phenol in cases where one of the latter reactions is used to prepare the 4-HAP. As more fully discussed below, this mole ratio may be, for example about 7 to 80.

The assisting solvent is an alkane having, for example about 4 to 16 carbon atoms and which may be straight chain, branched, or cyclic. Preferably, the assisting solvent is a straight chain alkane having 5 to 9 carbon atoms, most preferably 6 to 8 carbon atoms. Alkanes which may be used are for example, n-hexane, n-octane, 2,2,4-trimethylpentane ("isooctane"), n-heptane, n-pentane, n-nonane, n-decane and methylcyclopentane.

In general, a sufficient amount of alkane assisting solvent is used in the distillation vessel to provide for efficient separation of HF from 4-HAP with a minimum of 4-HAP degradation. Thus, the ratio of alkane assisting solvent to HF must be high enough to provide the latent heat necessary to volatilize the HF. In many cases, the quantity of assisting solvent is such that the assisting solvent/feed ratio (L/F) is at least about 1, preferably about 1 to 15, and most preferably about 2 to 5.

The distillation vessel is generally operated at a base temperature within a range, the minimum of which is at about the melting point of the mixture and the maximum of which is the temperature at which the 4-HAP significantly degrades. Suitably, the temperature is in the range of about 110° to 130°, preferably about 110° to 115° C., and the pressure is in the range of about 0.1 to 10 atm., preferably about 1 to 50 psig. In general, it is desirable for the pressure to be high enough to allow condensation of the HF in the overhead without refrigeration.

Any suitable distillation vessel may be used for purposes of this invention. Thus, the vessel may or may not contain interior surfaces serving to implement condensation and re-vaporization of the constituents of the composition being separated, e.g. packing, trays, and the like. For continuous or semi-continuous operation, the use of a fractionating column e.g. a packed column or a column containing trays is particularly suitable. When operating continuously, the feed composition and assisting solvent may be premixed before entering the column. Preferably, however, they are injected into the column at separate points.

The vapors comprising alkane and HF from the top of the column are condensed to form immiscible alkane and HF layers. The alkane condensate decanted from the HF layer may be returned to the column as reflux, with the column operating as a stripping column if the alkane is returned below the 4-HAP/HF feed point or as a normal column if returned above such feed point.

Molten 4-HAP and some alkane assisting solvent collect at the base of the distillation vessel and separate into two liquid phases since they are substantially immiscible. The alkane is decanted from the 4-HAP and recycled to the vessel, e.g. after reboiling, and the 4-HAP is removed for subsequent use or further purification. This mode of operation allows for economical use of the solvent without additional solvent separation/purification steps.

The distillation process of this invention is preferably integrated with a process for the production of 4-HAP by the Fries rearrangement of phenyl acetate or the Friedel-Crafts acetylation of phenol with acetic acid or anhydride, each process utilizing HF as a catalyst, as described for example in the previously-cited U.S. patent applications. In carrying out the reaction, the phenyl acetate, or phenol and acetylating agent, catalyst, and if desired when phenyl acetate is the starting material an additive for the reaction such as acetic anhydride or acetic acid, may be charged to a corrosion-resistant reactor and the mixture maintained at a temperature, for example, of about 20° to about 100° C. for a period, for example, of about ½ to about 4 hours, at a pressure, for example, of about 50 to about 500 psia. The HF may be charged as a liquid or a gas using technologies of handling well-known to those skilled in the art. In carrying out the reaction, an inert gas such as nitrogen may be used to keep the reaction space under the desired pressure and sufficient HF in contact with the reacting liquid. An excess of HF is generally used, for example, about 7 to about 80 moles per mole of phenyl acetate or phenol initially present in the reaction zone.

The solvent-assisted distillation of this invention may be carried out with or without a previous separation of some HF from the feed mixture in the absence of assisting solvent, e.g. by distillation under vacuum.

The invention is further illustrated by the following examples for which the general procedure for sample workup was as follows: Solutions of 4-HAP in HF, obtained by Fries rearrangement of phenyl acetate in the presence of HF as a catalyst or as a synthetic mixture of 4-HAP and HF, were subjected to the distillation conditions described. To obtain the results of the distillation, the 4-HAP-rich product was dissolved in ethyl acetate, transferred into ice water and titrated to pH of 7 with sodium or potassium hydroxide to determine the moles of HF present. The organic phase was separated. The aqueous layer was extracted with an additional portion of ethyl acetate and separated. The organic layers were combined, dried over MgSO$_4$, and evaporated.

Results of examples 1-12 inclusive are shown in Tables I and II, wherein column 1 shows compositions of the feed solution excluding HF (designated "A"), compositions of column product (designated "B"), and the difference between the two (designated "dif."), for each example. In addition to 4-HAP (normalized to 0% ethyl acetate) and PhOAc, the tables show weight percentages of 2-hydroxyacetophenone (2-HAP), phenol (PhOH), and ethyl acetate (EtOAc), present from the sample collection procedure, and also contain values for gas chromatography heavy ends (GC H.E.), gas chromatography accountability (GC Accnt.), L/F ratio (L/F), and parts per million of combined fluorine in the 4-HAP column product (F, ppm), determined either by ion chromotography or titration (indicated by "(t)").

Titration values were erratic and ion chromotograph values were believed to be more accurate.

EXAMPLES 1 TO 6

Solutions of 4-HAP and minor amounts of impurities in HF were obtained by means of the Fries rearrangement of phenyl acetate in the presence of HF as a catalyst. The reactor was a stirred autoclave equipped with ports in the head allowing for the addition of phenyl acetate (PhOAc), HF and solvents as well as nitrogen pressure and vacuum aspiration. A drain in the bottom allowed for product removal. HF was loaded into the reactor and warmed to 40° C. PhOAc was then pumped into the reactor in an amount such that the mole ratio of HF to PhOAc was 30:1 in Examples 1 to 5 and 10:1 in Example 6 and held at 50° C. for 1 hour in Examples 1 to 5 and 3 hours in Example 6. The reactor product solution was then fed at 1-10 g/min into a distillation column supplied with 4 feet of Teflon packing and 3 independent band heaters at the base, and containing refluxing n-hexane as assisting solvent. A differential-pressure cell monitored pressure drop from the top of the column to the top of the base. Pressure was controlled by motor valve or simple pressure regulator.

Light ends were taken overhead to a condenser and into a receiver where phasing of the solvent with HF took place. Condensed HF was collected in the receiver until after the run was finished. Solvent was taken back through a steam preheater to the column below the HF/4-HAP solution feed point thus causing the column to operate as a stripping column.

The HF/4-HAP feed stream entered the column near 30° C. while solvent was preheated to 90°-110° C. before being sent into the column. The rate of liquid solvent returned to the column from the overhead condenser was varied with HF feed to give the desired L/F ratio, i.e. liquid reflux/HF feed; hexane solvent return rates were generally 30-75 ml/min.

Product 4-HAP and condensed solvent traveled down the column to its base where they separated into two immiscible liquid phases, an n-hexane-rich phase which was decanted and vaporized in the reboiler for recycle to the base of the column, and a 4-HAP-rich product phase which was removed from the base at regular intervals. The column reboiler was generally operated at 120°-130° C., which required 40 psig for hexane. Results of the distillation are given in Table I.

TABLE I

| Example | 4-HAP | 2-HAP | PhOH | PhOAc | GC H.E. | EtOAc | GC Accnt. | L/F | F, ppm |
|---|---|---|---|---|---|---|---|---|---|
| 1A | 91.3 | 3.6 | 0.5 | — | 0.5 | 0.3 | 96 | | |
| 1B | 89.0 | 3.4 | 0.4 | — | 1.8 | 0.1 | 95 | 5.6 | 380 |
| dif. | −2.3 | −0.2 | −0.1 | 0.0 | +1.3 | | −1 | | |
| 2A | 92.5 | 4.1 | 1.2 | 0.1 | 0.5 | 2.9 | 99 | | |
| 2B | 91.4 | 4.4 | 1.0 | — | 1.4 | 1.5 | 98 | 5.5 | 330(t) |
| dif. | −1.1 | +0.3 | −0.2 | −0.1 | +0.9 | | −1 | | |
| 3A | 86.3 | 3.8 | 1.1 | — | 0.5 | 2.8 | 93 | | |
| 3B | 88.0 | 3.5 | 0.9 | — | 1.3 | 0.9 | 94 | 4.6-5.7 | 85 |
| dif. | +1.7 | −0.3 | −0.2 | 0.0 | +0.8 | | +1 | | |
| 4A | 89.6 | 3.5 | 0.8 | — | 0.4 | 0.4 | 95 | | |
| 4B | 88.6 | 3.6 | 0.9 | — | 1.5 | 0.3 | 94 | 4.3-6.4 | 690(t) |
| dif. | −1.0 | +0.1 | +0.1 | 0.0 | +1.1 | | −1 | | |
| 5A | 91.9 | 3.0 | 1.0 | — | 0.8 | 0.3 | 97 | | |
| 5B | 91.8 | 2.7 | 1.0 | — | 0.6 | 0.2 | 96 | 5.5-4.7 | 140(t) |
| dif. | −0.1 | +0.3 | 0.0 | 0.0 | −0.2 | | −1 | | |
| 6A | 83.3 | 4.6 | 1.1 | 0.3 | 5.4 | 0.5 | 95 | | |
| 6B | 83.4 | 4.5 | 1.5 | 0.1 | 3.7 | 1.6 | 94 | 4.2-4.4 | 1,300 |
| dif. | +0.1 | −0.1 | +0.4 | −0.2 | −1.7 | | −1 | | |

EXAMPLES 7 TO 12

The procedure of Examples 1 to 5 was followed except that the column was run as a normal rather than a stripping column in Examples 7 and 8, i.e. the n-hexane reflux was returned to column above rather than below the HF/4-HAP feed point, n-octane rather than n-hexane was employed as assisting solvent in Example 9, the column was run as a normal column and n-octane was the assisting solvent in Example 10, and the HF/4-HAP feed stream and n-hexane assisting solvent were premixed in Example 11 and 12. The results are shown in Table II.

TABLE II

| Example | 4-HAP | 2-HAP | PhOH | PhOAc | GC H.E. | EtOAc | GC Accnt. | ppm F | L/F |
|---|---|---|---|---|---|---|---|---|---|
| 7A | 91.0 | 3.6 | 2.1 | 0.5 | 0.4 | 1.3 | 98 | | |
| 7B | 94.5 | 2.7 | 1.0 | — | 0.9 | 0.6 | 99 | 310 | 16.7 |
| 8A | 90.1 | 4.1 | 1.1 | — | 0.4 | 0.6 | 96 | | |
| 8B | 89.6 | 1.8 | 0.9 | — | 1.1 | 0.1 | 94 | 201 | 2.6-4.0 |
| 9A | 90.1 | 4.4 | 1.0 | 0.1 | 1.1 | 2.4 | 97 | | |
| 9B | 87.1 | 3.6 | 0.3 | 0.1 | 3.7 | 0.6 | 95 | −50(t) | 8 |
| 10A | 94.7 | 3.6 | 1.1 | — | 0.6 | 0.1 | 101 | | |
| 10B | 92.6 | 2.0 | 0.1 | — | 1.3 | 0.2 | 96 | 210 | 5 |
| 11A | 90.8 | 4.4 | 0.7 | — | 3.9 | 0.5 | 100 | | |
| 11B | 88.9 | 4.0 | 0.6 | — | 2.8 | 0.6 | 96 | 1,200(t) | 8 |
| 12A | 90.6 | 4.4 | 0.6 | 0.6 | 0.6 | 0.3 | 95 | | |
| 12B | 92.4 | 1.8 | 0.5 | — | 0.9 | 0.5 | 95 | 3,300 | 5.6 |

EXAMPLES 13 TO 23

These examples illustrate the alkane solvent assisted distillation of mixtures of 4-HAP, HF and in some cases acetic acid with or without water. In Examples 13 to 20, 22 and 23 the feed mixtures were synthetically prepared while in Example 21, the feed was prepared by the acetylation of phenol with acetic anhydride using HF as catalyst, as described in previously cited applications Ser. Nos. 06/714,407 and 06/721,007, wherein the mole ratio of phenol: anhydride: HF was 1:1:30, the reaction temperature was 73°–82° C. and the reaction time was one hour. In Examples 13, 14 and 16 to 21, the assisting solvent was n-octane, in Example 15, the solvent was an isooctane/n-octane solvent mix and in Examples 22 and 23, the solvent was n-hexane.

The distillation vessel was a tubular column containing polyethylene packing. Heating was accomplished using heating tape adapted with feed points for solvent and HF/4-HAP just above the packing. There was no rectification above the feed points. Distillate brought overhead was cooled in a condenser with refrigerated water prior to collection in an iced knock-out pot. Pressure was regulated using a water aspirator with a nitrogen bleed. The solvent was charged into the base of the column and brought to reflux at ca. 633 mm Hg. absolute. Solvent was then fed at a selected rate of 3–6 ml/min to match the rate of solvent distilled overhead using the heat input to control distillation. When the solvent feed rate was equivalent to the rate of distillation, solvent feed was ceased. The 4-HAP/HF feed was then added at the same preselected feed rate as was the solvent. 4-HAP/HF feed was added for 20 minutes; additional solvent was not added unless the thermocouples placed on the skin of the base of the column indicated that the base was dry. At the end of 4-HAP/HF addition, the feed was switched back to solvent and allowed to reequilibrate. The column residue was drained into ice water, neutralized and analyzed.

Results of these examples are given in Table III which shows the compositions of feed and residue, feed rate, overhead temperature and 4-HAP accountability. The latter values were determined by dissolving all the deposits formed on the column packing and surfaces with ethyl acetate, adding the 4-HAP in these deposits to that in the column residue and that left in the feed vessel, and calculating the total as a percentage of the 4-HAP in the original feed sample. The residue mole ratio in Example 21 is of 4-HAP to total acid (HF plus acetic acid).

To a stirred autoclave were added either solid 4-HAP and HF to form a synthetic mixture (Examples 24 and 25) or a "live" 4-HAP formed as the product of a Fries rearrangement of phenyl acetate using HF as a catalyst following the procedure of Examples 1 to 6 except that the reaction temperature was 40° C. (Examples 26 and 27). In Examples 24 and 25, the mixture was allowed to warm to room temperature with stirring and nitrogen was added to bring the pressure to 5 psig. In Examples 26 and 27, the feed was vented through a scrubber containing potassium hydroxide with a nitrogen purge for ca. 1 hour at 30°–40° C. prior to batch distillation. The solvent was added last (after excess HF had been vented for live 4-HAP samples). During the course of the distillation additional amounts of solvent were added as needed in an attempt to keep some solvent in the autoclave at all times.

The reactor was then evacuated through two scrubbers containing potassium hydroxide solution using a water aspirator vacuum of 62 mm Hg absolute. When violent bubbling in the scrubbers subsided, the reactor was heated to 40° C. with continued stirring. Generally, bubbling in the scrubbers subsided after 20 minutes of heating at 30°–40° C.

Continued heating with increasing temperature resulted in removal of additional HF. After the desired heating period had been reached, the reactor was cooled to ca. 0° C. and pressured to atmospheric pressure with nitrogen. The solid residue was dissolved in ethyl acetate (50 ml), transferred into ice water (100 ml) and titrated to pH 7 with a known amount of sodium or potassium hydroxide to determine the moles of HF present. The organic phase was separated. The aqueous layer was extracted with an additional portion (25 ml) of ethyl acetate and separated. The organic layers were combined, washed with a saturated sodium chloride solution, dried over MgSO$_4$, and evaporated.

Table IV shows for each example the compositions of the initial and final mixtures and the quantity of 4-HAP or the total charge in the initial mixture, the identifica-

TABLE III

| Example | Feed 4-HAP:HF:HOAc:H2O Mole Ratio | Feed Rate (ml/min) | Overhead Temperature (633 mm Hg) | % 4-HAP Accountability | Residue 4-HAP:HF:HOAc Mole Ratio |
| --- | --- | --- | --- | --- | --- |
| 13 | 1:10:0:0 | 6.6 | 88–55° C. | — | 5.1:1.0:0 |
| 14 | 1:10:0:0 | 6 to 2.5 | 114–70° C. | 73 | 0.5:1.0:0 |
| 15 | 1:10:0:0 | 6.6 | 88–41° C. | 92 | 3.7:1.0:0 |
| 16 | 1:10:0:0 | 3.4 | 94–73° C. | 92 | 2.6:1.0:0 |
| 17 | 1:4:0:0 | 3.0 | 104–83° C. | 100 | 18:1.0:0 |
| 18 | 1:25:1:1 | 3.0 | 100–70° C. | 94 | 40:1.0:0 |
| 19 | 1:25:1:0 | 3.0 | 99–68° C. | 96 | 23:1.0:2.4 |
| 20 | 1:5:1:0 | 3.0 | 103–73° C. | 92 | 14:1.0:1.6 |
| 21 | 1:30:1:0 | 3.0 | 94–67° C. | 88 | 33:1.0 |
| 22 | 1:25:1:1 | 3.3 | 51–32 | 93.6 | 1.0:0.4:0.5 |
| 23 | 1:5:1:1 | 3.4 | 62–49 | 94.1 | 1.0:0.5:0.4 |

EXAMPLES 24 TO 27

These examples illustrate the batch distillation of 4-HAP/HF mixtures using an alkane assisting solvent.

tion and quantity of assisting solvent, the stripping or distillation conditions and the percent 4-HAP recovered, calculated based on gas chromatographic analysis and the isolated mass.

TABLE IV

| Example | Initial 4-HAP:HF Mole Ratio | Organic Solvent | Stripping Conditions | Final 4-HAP:HF Mole Ratio | %-4-HAP Recovered |
| --- | --- | --- | --- | --- | --- |
| 24 | 1:1 (50.0 g 4-HAP) | n-Octane (50 ml) | 50–111° C./20 Min | 6.3:1.0 | 101% |
| 25 | 1:10 (40.5 g 4-HAP) | n-Octane (75 ml) | 50–120° C./20 Min | 5.1:1.0 | 85% |
| 26 | 1:10 | n-Octane | 40° C./1 Hr | 11.3:1.0 | 90% |

TABLE IV-continued

| Example | Initial 4-HAP:HF Mole Ratio | Organic Solvent | Stripping Conditions | Final 4-HAP:HF Mole Ratio | %-4-HAP Recovered |
|---|---|---|---|---|---|
| 27 | (40.5 g PhOAc) 1:10 (40.5 g PhOAc) | (95 ml) n-Heptane (80 ml) | 40° C./1 Hr 50–82° C./30 min | 5.8:1.0 | 83% |

In Examples 24 to 27, the condensate from the autoclave separated into immiscible solvent-rich and HF-rich phases. Furthermore, these examples could be operated so that some solvent-rich phase remained in the autoclave after the distillation which is immiscible with the 4-HAP-rich phase. Such solvent-rich phase could be decanted from the 4-HAP-rich phase without additional solvent separation-purification steps.

The results of Examples 1 to 27 show that the process of this invention can be used to separate efficiently most of the HF from 4-HAP/HF mixtures without appreciable degradation of the 4-HAP.

We claim:

1. A process comprising distilling a composition containing 4-hydroxyacetophenone and hydrogen fluoride in the presence of an alkane assisting solvent having from 4 to 16 carbon atoms to obtain an overhead vapor containing alkane solvent and most of the hydrogen fluoride in the feed and a liquid residue which separates into two immisicible phases, one containing most of the 4-hydroxyacetophenone in the feed and the other a preponderance of alkane solvent, separating said immiscible phases in the residue and recovering the 4-hydroxyacetophenone phase, condensing said overhead vapor to form two immiscible liquid phases, one containing a preponderance of hydrogen fluoride and the other a preponderance of alkane solvent, and returning the alkane solvent phase in the overhead condensate to said distillation as reflux.

2. The process of claim 1 wherein said alkane contains 6 to 8 carbon atoms.

3. The process of claim 2 wherein said alkane solvent is n-hexane.

4. The process of claim 2 wherein said alkane solvent is n-octane.

5. The process of claim 1 wherein said distillation process is operated at a solvent reflux/feed ratio of at least about 1.

6. The process of claim 5 wherein said distillation process is carried out in a fractionating column containing added internal surfaces to implement vaporization and condensation and said alkane solvent is returned to said column at a point below the introduction of the feed composition.

7. A process comprising subjecting phenyl acetate to a Fries rearrangement in the presence of hydrogen fluoride as catalyst to obtain a reaction product containing 4-hydroxyacetophenone and hydrogen fluoride and distilling said reaction product in the presence of an alkane solvent having from 4 to 16 carbon atoms to obtain an overhead vapor containing alkane solvent and most of the hydrogen fluoride in the reaction product and a liquid residue which separates into two immiscible phases, one containing most of the 4-hydroxyacetophenone in the reaction product, and the other a preponderance of alkane solvent, separating said immiscible phases in the residue and recovering the 4-hydroxyacetophenone phase, condensing said overhead vapor to form two immiscible liquid phases, one containing a preponderance of hydrogen fluoride and the other a preponderance of alkane solvent, and returning the alkane solvent phase in the overhead condensate to said distillation as reflux.

8. The process of claim 7 wherein said alkane contains 6 to 8 carbon atoms.

9. The process of claim 8 wherein said alkane solvent is n-hexane.

10. The process of claim 7 wherein said hydrogen fluoride-rich phase in said overhead condensate is recycled to said Fries rearrangement.

11. A process comprising subjecting phenol to a Friedel-Crafts acetylation with acetic acid or acetic anhydride as acetylating agent in the presence of hydrogen fluoride as catalyst to obtain a reaction product containing 4-hydroxyacetophenone and hydrogen fluoride, and distilling said reaction product in the presence of an alkane solvent having from 4 to 16 carbon atoms to obtain an overhead vapor containing alkane solvent and most of the hydrogen fluoride in the reaction product and a liquid residue which separates into two immiscible phases, one containing most of the 4-hydroxyacetophenone in the reaction product, and the other a preponderance of alkane solvent, separating said immiscible phases in the residue and recovering the 4-hydroxyacetophenone phase, condensing said overhead vapor to form two immiscible liquid phases, one containing a preponderance of hydrogen fluoride and the other a preponderance of alkane solvent, and returning the alkane solvent phase in the overhead condensate to said distillation as reflux.

12. The process of claim 11 wherein said alkane contains 6 to 8 carbon atoms.

13. The process of claim 12 wherein said alkane solvent is n-hexane.

14. The process of claim 11 wherein said hydrogen fluoride-rich phase in said overhead condensate is recycled to said Friedel-Crafts acetylation.

* * * * *